(12) United States Patent  
Nishino (10) Patent No.: US 7,956,330 B2
(45) Date of Patent: Jun. 7, 2011

(54) RADIATION IMAGING APPARATUS AND CRADLE

(75) Inventor: Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

(21) Appl. No.: 12/393,044

(22) Filed: Feb. 26, 2009

(65) Prior Publication Data

US 2010/0044572 A1 Feb. 25, 2010

(30) Foreign Application Priority Data

Mar. 7, 2008 (JP) .................................. 2008-057999

(51) Int. Cl.
*H01L 27/146* (2006.01)

(52) U.S. Cl. .................... 250/370.09; 320/115; 320/138; 320/DIG. 11

(58) Field of Classification Search ................... 320/138, 320/115, DIG. 11; 250/370.09
See application file for complete search history.

(56) References Cited

U.S. PATENT DOCUMENTS

| | | | |
|---|---|---|---|
| 7,119,304 B2 * | 10/2006 | Meyers | 219/204 |
| 2006/0054829 A1 * | 3/2006 | Tsuchino et al. | 250/370.09 |
| 2006/0103355 A1 * | 5/2006 | Patino et al. | 320/138 |
| 2007/0188136 A1 * | 8/2007 | Oh | 320/115 |
| 2008/0029707 A1 * | 2/2008 | Kari et al. | 250/370.09 |
| 2008/0169420 A1 * | 7/2008 | Eguchi | 250/370.09 |

FOREIGN PATENT DOCUMENTS

| | | |
|---|---|---|
| JP | 2001-224579 | 8/2001 |
| JP | 3494683 B2 | 2/2004 |
| JP | 2005-7086 | 1/2005 |

* cited by examiner

*Primary Examiner* — Constantine Hannaher
(74) *Attorney, Agent, or Firm* — Solaris Intellectual Property Group, PLLC (57) ABSTRACT

Closeness of a housing is maintained in a normal handling state, and electric power shortage is solved to perform prompt action by quick charge in emergency situations. Normally an electronic cassette is loaded in a cradle to charge a battery by a non-contact charging function. In a case of contact charge, a pair of electrodes and a pair of terminals are brought into contact with each other by removing a packing, and the battery is charged in a state where wiring is physically connected. Therefore, energy efficiency is better compared with the non-contact charge, and the charge can be performed in a short time.

12 Claims, 7 Drawing Sheets

RADIATION IMAGING APPARATUS AND CRADLE

CROSS-REFERENCE TO RELATED APPLICATION

This application claims priority under 35 USC 119 from Japanese Patent Application No. 2008-057999, the disclosure of which is incorporated by reference herein.

BACKGROUND OF THE INVENTION

1. Field of the Invention

The present invention relates to a radiation imaging apparatus in which at least an imaging plate, an image data memory, and a power supply unit are accommodated in a closed housing, and a cradle in which the radiation imaging apparatus is accommodated. The imaging plate, in which pixels in which charges are accumulated by receiving a radiation are two-dimensionally arrayed, takes an image based on the radiation. The image data memory stores data of the image taken by the imaging plate. The power supply unit supplies an electric power to the imaging plate and the image data memory.

2. Related Art

For example, Japanese Patent No. 3494683 discloses a radiation imaging apparatus (also referred to as a cassette for radiation detector or electronic cassette) in which a radiation detector and an image memory are incorporated. In the electronic cassette, a radiation image detected by the radiation detector is stored as image data in the image memory, the image data read from the image memory is converted into a wireless signal, and the wireless signal is output to an external signal processing circuit.

Because the electronic cassette is used in medical field, the housing has an closed structure from the standpoints of good hygiene and radiation handling. For example, Japanese Patent Application Laid-Open (JP-A) No. 2001-224579 discloses the closed structure.

On the other hand, the electronic cassette requires a measurable amount of electric power, it is necessary to reduce the power consumption. For example, JP-A No. 2005-7086 proposes a technique for the purpose of the reduction of the power consumption. In the technique, a capacitance amount of a battery provided in the closed structure is monitored, and the electronic cassette switches to a power saving mode to avoid the unnecessary power consumption when the capacitance amount becomes a predetermined value or less.

However, sometimes the electronic cassette is suddenly used in an emergency in the field of emergency medical care. In such emergency situation, unfortunately a response to the emergency situation cannot be given unless the battery of the electronic cassette is sufficiently charged. One of the reasons why the response to the emergency situation cannot be given is that quick charge cannot be performed, because, if the housing of the electronic cassette has the closed structure, the battery is inevitably charged by non-contact charge.

Even if the electronic cassette switches to the power saving mode due to the decreased capacitance amount of the battery, a battery lifetime is merely lengthened in the state of the decreased capacitance amount of the battery, and the response to the emergency situation is insufficiently given.

SUMMARY OF THE INVENTION

In view of the foregoing, an object of the present invention is to provide a radiation imaging apparatus in which the closeness of the housing can be maintained in the normal handling state while the electric power shortage can be solved by quick charge so as to perform prompt action in emergency situation, and a cradle.

A first aspect of the invention provides a radiation imaging apparatus in which at least an imaging plate in which pixels which accumulate charges by receiving radiation are two-dimensionally arrayed, and which takes an image based on the received radiation, an image data memory in which data of the image taken by the imaging plate is stored, and a power supply unit that supplies electric power to the imaging plate and the image data memory, are accommodated in a closed housing, the radiation imaging apparatus including: a secondary coil unit provided in the housing and constituting a part of a non-contact type charging device, the secondary coil unit receiving an electric power by an electromagnetic induction effect between the secondary coil unit and a primary coil unit provided outside the housing; a terminal provided in the power supply unit, a leading end portion of which is projected outside the housing so as to be able to electrically contact an electrode of a contact type charging device provided outside the housing; and a closing member that is attachable to and detachable from the housing so as to be able to expose and close off the leading end portion of the terminal from the outside, the closing member maintaining a closed state of the housing when being attached to the housing, and putting the leading end portion of the terminal into an exposed state when being detached from the housing.

Accordingly, in the first aspect of the invention, the closeness of the housing is maintained because the charge can be performed by an electromagnetic induction effect using the secondary coil unit. In emergency situations, the terminal is brought into electric contact with the electrode of the external charging device, so that the charge can be performed faster than that due to the electromagnetic induction effect. Because the radiation imaging apparatus has both charge functions, the closing member can close the surroundings of the terminal to maintain the closeness of the housing in the normal state, and the closing member can be removed to establish the electric contact (connection) between the terminal and the electrode in order to rapidly perform the charge in the emergency situation.

The meaning of projection of the terminal includes not only the projection of the terminal from the outline or profile ("silhouette") of the housing but also the projection of the terminal within a recess region of a recess portion formed in a part of the housing. In a case where the terminal is projected within the recess portion formed in a part of the housing, although the terminal is not projected on the outline of the housing, the terminal is actually projected from the housing.

In accordance with a second aspect of the invention, in the radiation imaging apparatus of the first aspect, the power supply unit includes: a quick charging section that performs a quick charge mode for performing quick charging; and a normal charging section that performs a normal charge mode for performing non-quick charging, contact charging by electrical contacting of contact-points is at least performed in the quick charge mode, and non-contact charging is performed in the normal charge mode.

Accordingly, in the second aspect of the invention, the quick charge can be performed because the quick charging section is used when the charge is performed by the electric connection between the terminal and the electrode.

Examples of the quick charging section include a nickel-cadmium battery, a nickel-hydrogen battery, and a capacitor (electric double layer capacitor).

In accordance with a third aspect of the invention, in the radiation imaging apparatus of the second aspect, switching between the quick charging section and the normal charging section is performed by attaching and detaching the closing member.

Accordingly, in the third aspect of the invention, when the closing member closes the surroundings of the terminal, the radiation imaging apparatus inevitably becomes the normal charge mode because the terminal is hidden. On the other hand, when the closing member is removed, the charge can be performed by at least the contact charge (quick charge mode) because the exposed terminal is brought into electric contact with the electrode.

When switching the radiation imaging apparatus to the contact charge, the normal charge mode (non-contact charge) may be combined.

In accordance with a fourth aspect of the invention, in the radiation imaging apparatus of the second aspect, switching between the quick charging section and the normal charging section is performed based on electrical contact between the terminal and the electrode provided outside the housing, the quick charge mode is performed when the electrical contact is detected, and the normal charge mode is performed when the electrical contact is not detected.

Accordingly, in the fourth aspect of the invention, automatic switching can be performed by detecting the electric contact state between the terminal and the electrode.

In accordance with a fifth aspect of the invention, in the radiation imaging apparatus of the first aspect, a recess portion is formed surrounding the terminal, and the closing member is attachable to the recess portion.

In accordance with a sixth aspect of the invention, in the radiation imaging apparatus of the first aspect, the closing member is connected to the housing via a connecting member.

In accordance with a seventh of the invention, in the radiation imaging apparatus of the second aspect, the contact charging and the non-contact charging are performed in the quick charge mode.

In accordance with an eighth aspect of the invention, in the radiation imaging apparatus of the second aspect, the non-contact charging is performed by the primary coil unit provided outside the housing and the secondary coil unit provided in the housing constituting parts of the non-contact type charging device, and the contact charging is performed by contacting the leading end portion of the terminal and the electrode of the contact type charging device provided outside the housing.

A ninth aspect of the invention provides a radiation imaging apparatus in which at least an imaging plate in which pixels which accumulate charges by receiving radiation are two-dimensionally arrayed, and which takes an image based on the received radiation, an image data memory in which data of the image taken by the imaging plate is stored, and a power supply unit that supplies electric power to the imaging plate and the image data memory, are accommodated in a closed housing, the radiation imaging apparatus including: a secondary coil unit provided in the housing and constituting a part of a non-contact type charging device, the secondary coil unit receiving electric power by an electromagnetic induction effect between the secondary coil unit and a primary coil unit provided outside the housing; and a connect terminal formed in the housing so as to be able to maintain a closed state of the housing, that is connected to the power supply unit and connected to the image data memory such that the data can be accessed from outside the housing, wherein contact charging can be performed via the connect terminal by a contact type charging device provided outside the housing.

In accordance with a tenth aspect of the invention, in the radiation imaging apparatus of the ninth aspect, the radiation imaging apparatus further includes a closing member that is attachable to and detachable from the housing so as to be able to expose and close off the contact terminal from the outside.

In accordance with an eleventh aspect of the invention, in the radiation imaging apparatus of the ninth aspect, the contact terminal is a USB terminal.

In accordance with a twelfth aspect of the invention, in the radiation imaging apparatus of the ninth aspect, the contact terminal is an IEEE 1394 standard terminal.

An thirteenth aspect of the invention provides a cradle in which a radiation imaging apparatus in which at least an imaging plate in which pixels which accumulate charges by receiving radiation are two-dimensionally arrayed, and which takes an image based on the received radiation, an image data memory in which data of the image taken by the imaging plate is stored, and a power supply unit that supplies electric power to the imaging plate and the image data memory, are accommodated in a closed housing, is accommodated, the radiation imaging apparatus including: a secondary coil unit provided in the housing and constituting a part of a non-contact type charging device, the secondary coil unit receiving an electric power by an electromagnetic induction effect between the secondary coil unit and a primary coil unit provided outside the housing; a terminal provided in the power supply unit, a leading end portion of which is projected outside the housing so as to be able to electrically contact an electrode of a contact type charging device provided outside the housing; and a closing member that is attachable to and detachable from the housing so as to be able to expose and close off the leading end portion of the terminal from the outside, the closing member maintaining a closed state of the housing when being attached to the housing, and putting the leading end portion of the terminal into an exposed state when being detached from the housing, wherein an accommodation unit in which the radiation imaging apparatus is accommodated is provided, the primary coil unit is disposed at a position in which the primary coil unit faces the secondary coil unit when the radiation imaging apparatus is accommodated in the accommodation unit, the electrode is disposed so as to be able to electrically contact the leading end portion of the terminal when the radiation imaging apparatus is accommodated in the accommodation unit, and when accommodating the radiation imaging apparatus in the accommodation unit, the non-contact charging is applied when the closing member closes off the leading end portion of the terminal, and the contact charging is applied when the closing member exposes the leading end portion of the terminal.

According to the eleventh aspect of the invention, the non-contact charge is applied by the electromagnetic induction between the secondary coil unit and the primary coil unit when the closing member is attached to the surroundings of the terminal to close the terminal, and the contact charge establishing the electric connection between the terminal and the electrode is applied when the closing member is removed to expose the terminal.

Thus, the invention can provide the radiation imaging apparatus in which the closeness of the housing can be maintained in the normal handling state while the electric power shortage is solved to perform prompt action by quick charge in emergency situation, and the cradle.

BRIEF DESCRIPTION OF THE DRAWINGS

Exemplary embodiments of the present invention will be described in detail with reference to the following figures, wherein:

FIGS. 5A and 5B are a front view showing a state in which the electronic cassette is inserted in the cradle of the exemplary embodiment.

FIGS. 6A and 6B are an enlarged view showing a contact charge of the exemplary embodiment.

DETAILED DESCRIPTION OF THE INVENTION

Figure 1:
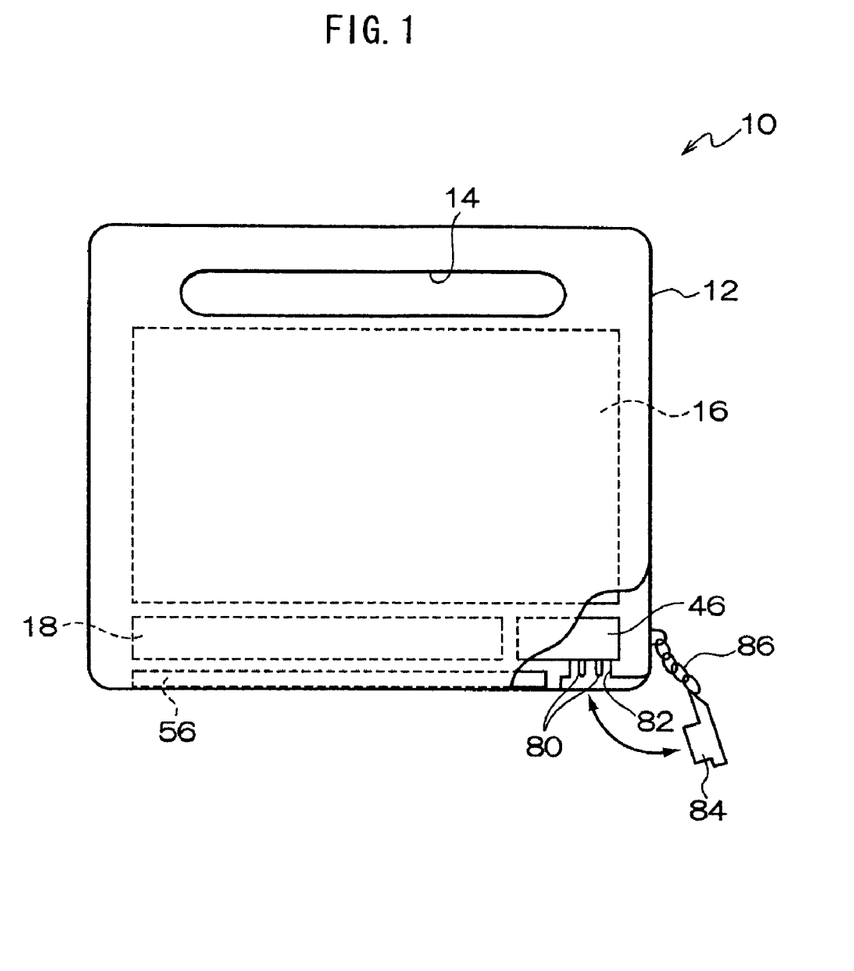
FIG. 1 is a schematic diagram showing an electronic cassette according to an exemplary embodiment of the invention.

FIG. 1 shows an electronic cassette 10 according to an exemplary embodiment of the present invention. The electronic cassette 10 is covered with a housing 12 such that functional components accommodated in the electronic cassette 10 are closed (sealed).

A long hole 14 pierced through a front side and a back side of the housing 12 is made in the housing 12, and a user can grasp the electronic cassette 10 with fingers inserted in the long hole 14.

The functional components are roughly classified into an imaging plate 16 and an image memory 18. The imaging plate 16 takes a radiation image, and the radiation image taken by the imaging plate 16 is stored in the image memory 18.

Figure 2:
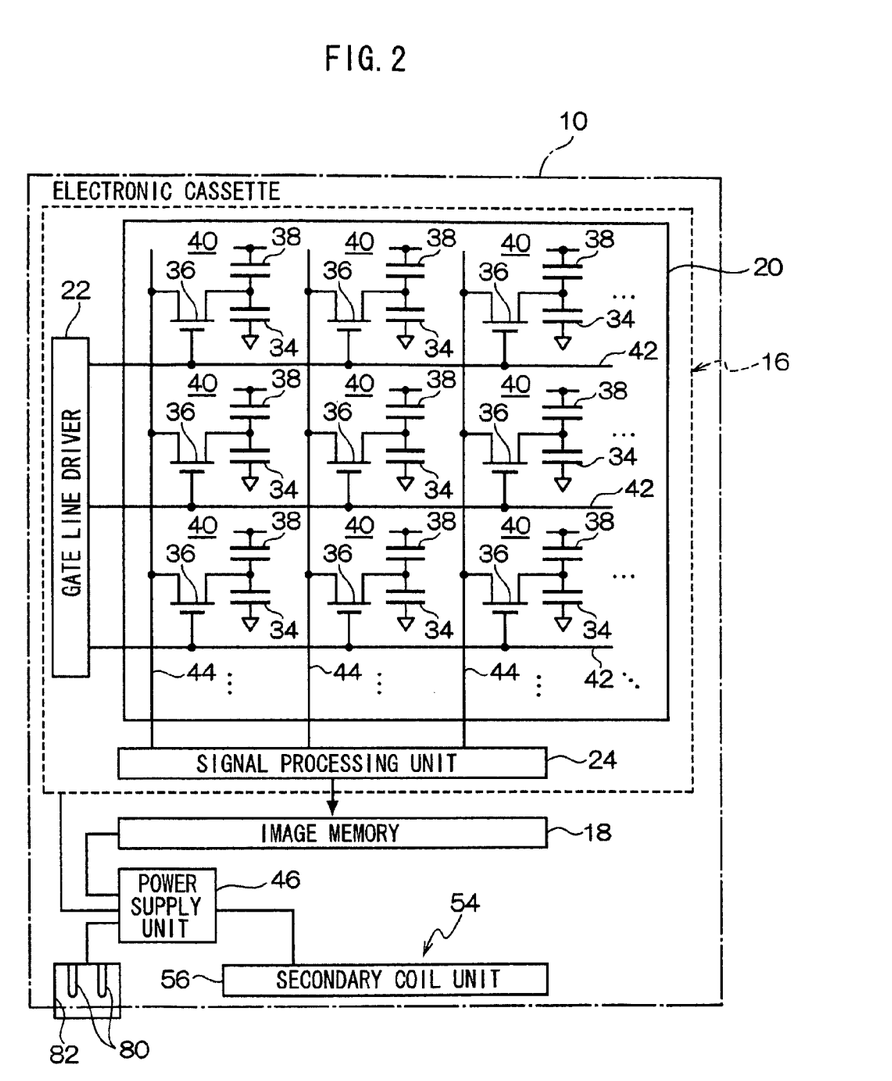
FIG. 2 is a block diagram showing a schematic configuration of the electronic cassette of the exemplary embodiment.

As shown in FIG. 2, the imaging plate 16 includes a TFT active matrix substrate (board) 20, a gate line driver 22, and an image processing unit 24. A matrix interconnection pattern is formed by the gate line driver 22 and the image processing unit 24, and the gate line driver 22 and the image processing unit 24 control an operation of TFT (Thin Film Transistor) provided at each intersecting point of the interconnections.

Figure 3:
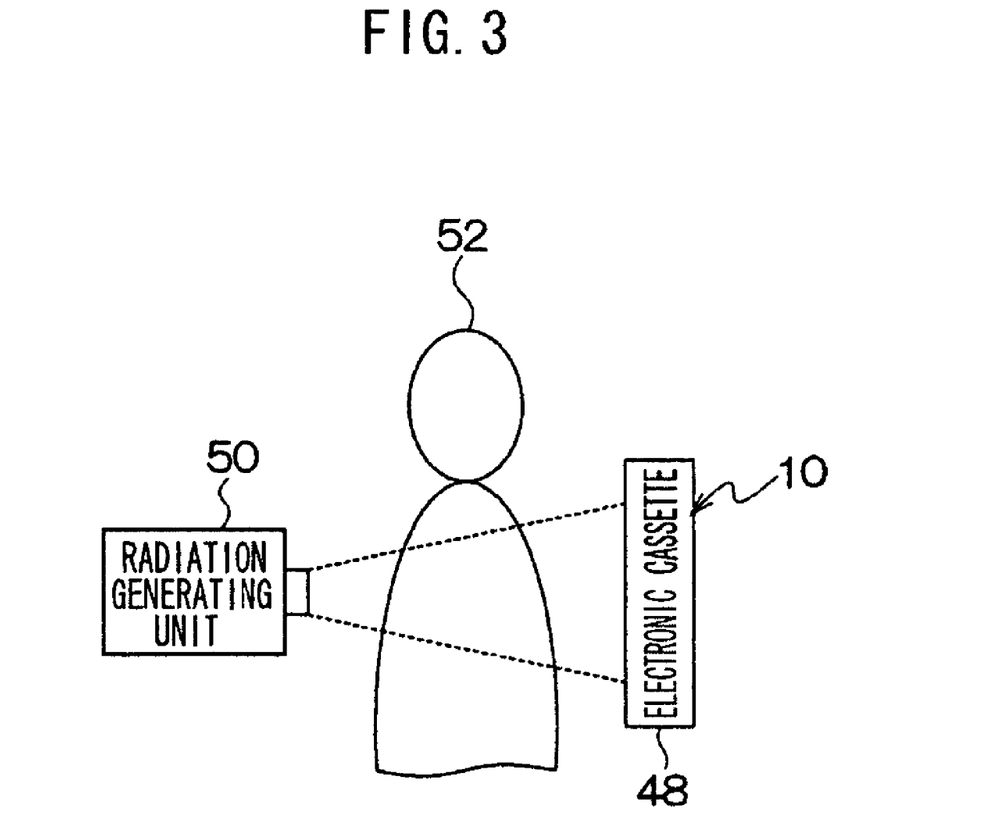
FIG. 3 is a diagram showing a method for using the electronic cassette of the exemplary embodiment.

As shown in FIG. 3, the radiation is emitted from a radiation generating unit 50, a subject 52 is projected onto an imaging surface 48 in the housing 12 of the electronic cassette 10, and the projected image is taken as the radiation image by the imaging plate 16.

(Detailed Configuration of Imaging Plate)

A configuration of an electric system of the electronic cassette 10 will be described below. The imaging plate 16 of the electronic cassette 10 is formed by laminating a photoelectric conversion layer on the TFT active matrix board 20. The photoelectric conversion layer absorbs the radiation to convert the radiation into charges. For example, the photoelectric conversion layer is made of a-Se (amorphous selenium) mainly containing selenium (for example, content rate of 50% or more). When the photoelectric conversion layer is irradiated with the radiation, the photoelectric conversion layer generates at the inside charges (electron-hole pairs) of amount according to the amount of radiation with which the photoelectric conversion layer is irradiated, thereby converting the radiation into the charges. Many pixel portions 40 (in FIG. 2, a portion of the photoelectric conversion layer corresponding to the individual pixel portion 40 is schematically shown as a photoelectric conversion unit 38) are disposed into a matrix manner on the TFT active matrix board 20. The pixel portion 40 includes an accumulation capacitor 34 and a TFT 36. The charges generated in the photoelectric conversion layer are accumulated in the accumulation capacitor 34. TFT 36 reads the charges accumulated in the accumulation capacitor 34. The charges generated in the photoelectric conversion layer in association with the irradiation of the electronic cassette 10 with the radiation are accumulated in the respective accumulation capacitors 34 of the individual pixel portions 40. Therefore, the image information carried by the radiation with which the electronic cassette 10 is irradiated is converted into charge information and held by the TFT active matrix board 20.

Plural gate interconnections (lines) 42 and plural data interconnections (lines) 44 are provided in the TFT active matrix board 20. The gate interconnections 42 are used to individually turn on and off TFTs 36 of the pixel portions 40 extended in a predetermined direction (row direction). The data interconnections 44 are used to read the charges accumulated in the accumulation capacitors 34 through the turned-on TFTs 36 extended in a direction (column direction) orthogonal to the gate interconnections 42. Each of the gate interconnections 42 is connected to the gate line driver 22, and each of the data interconnections 44 is connected to the image processing unit 24. When the charges are accumulated in the accumulation capacitor 34 in each pixel portion 40, the TFTs 36 of the pixel portions 40 are sequentially turned on in unit of row by signals supplied from the gate line driver 22 through the gate interconnection 42, and the charges accumulated in the accumulation capacitor 34 of the pixel portion 40 where TFT 36 is turned on are transmitted as a charge signal through the data interconnection 44 and input into the image processing unit 24. Accordingly, the charges accumulated in the accumulation capacitors 34 of the pixel portions 40 are sequentially read in unit of row.

Although not shown in the drawings, the image processing unit 24 includes amplifiers and sample-hold circuits. The amplifier and the sample-hold circuit are provided in each of the data interconnections 44. The charge signal transmitted through each data interconnection 44 is held by the sample-hold circuit after being amplified by the amplifier. A multiplexer and an A/D converter are sequentially connected onto an output side of the sample-hold circuit, the charge signal held by each sample-hold circuit is sequentially (serially) input into the multiplexer, and the charge signal is converted into digital image data by the A/D converter. The image memory 18 is connected to the image processing unit 24, and the image data output from the A/D converter of the image processing unit 24 are sequentially recoded in the image memory 18. The image memory 18 has a storage capacity in which pieces of image data corresponding to plural frames can be stored, and the pieces of image data obtained by taking the radiation image are sequentially stored in the image memory 18.

An electric power is required to take the radiation image in the imaging plate 16 and to store the radiation image in the image memory 18. The electric power is supplied from a power supply unit 46 provided in an inner space of the housing 12. In other words, the power supply unit 46 is placed in an environment isolated completely from the outside.

The power supply unit 46 is appropriately charged by a non-contact charging device 54. The non-contact charging device 54 is operated based on a principle of IPT (Induction Power Transmission).

IPT means a charging system in which an electromagnetic induction phenomenon is utilized. In IPT, the charge is performed without bringing metals such as a cable, a plug, and a pantograph into contact with each other. Specifically, a magnetic flux generated from a primary coil is received by a secondary coil through a core.

As shown in FIGS. 1 and 2, a secondary coil unit 56 of the charging device 54 is provided in a bottom portion (an opposite side to the side on which the long hole 14 is made) of the housing 12. A primary coil unit 58 is disposed in a pocket unit 62 of a cradle 60 which will be mentioned later (see FIG. 5).

Figure 4A:
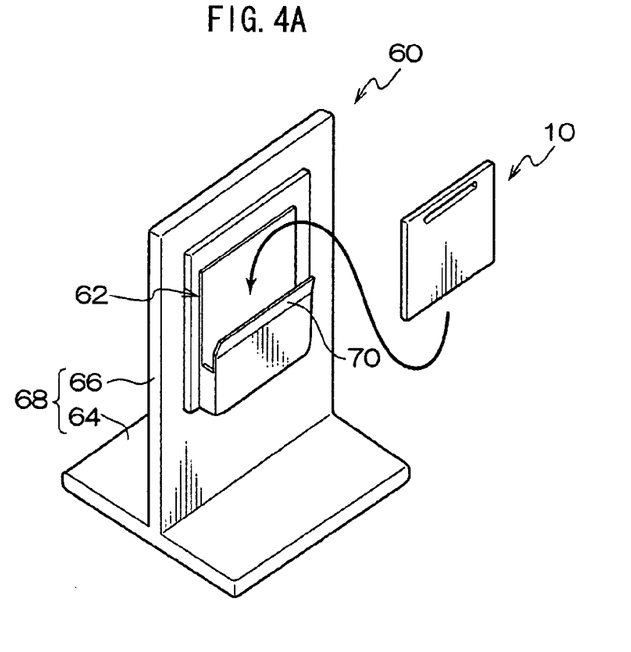
FIGS. 4A and 4B are perspective views showing the electronic cassette and a cradle of the exemplary embodiment.

FIG. 4A shows the cradle 60 in which the electronic cassette 10 is accommodated and retained. The cradle 60 includes a stand 68, and the stand 68 includes a rectangular base 64 and a vertical wall portion 66 which is vertically provided from an upper surface of the base 64. The vertical wall portion 66 of the stand 68 has a pocket unit 62 at one of surfaces of the vertical wall portion 66. The pocket unit 62 has a box shape whose top portion is opened, an inside dimension in a thickness direction is slightly larger than a thickness of the electronic cassette 10. The electronic cassette 10 can be accommodated in the box-shape pocket unit 62.

Figure 4B:
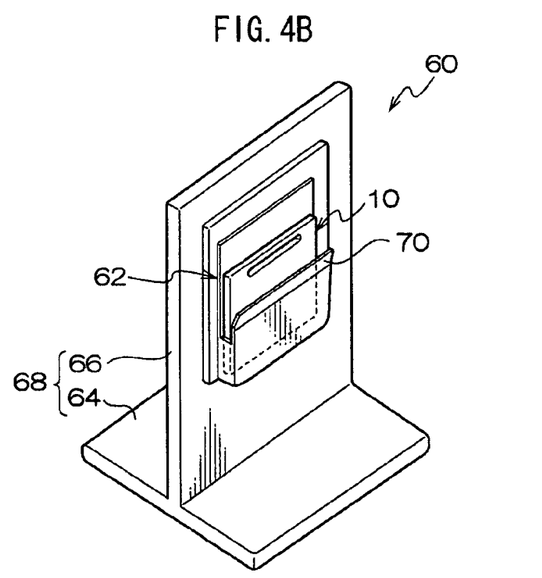

A bend portion 70 which is bent is formed in an upper end portion of a wall surface on the front side in the thickness direction such that the opening is enlarged. The bend portion 70 also acts as a guide surface when the electronic cassette 10 is inserted in the pocket unit 62. Therefore, the electronic cassette 10 is smoothly accommodated in the pocket unit 62. The electronic cassette 10 is accommodated in the pocket unit 62 such that the secondary coil unit 56 is located on the lower side (see FIG. 4B).

Figure 5A:
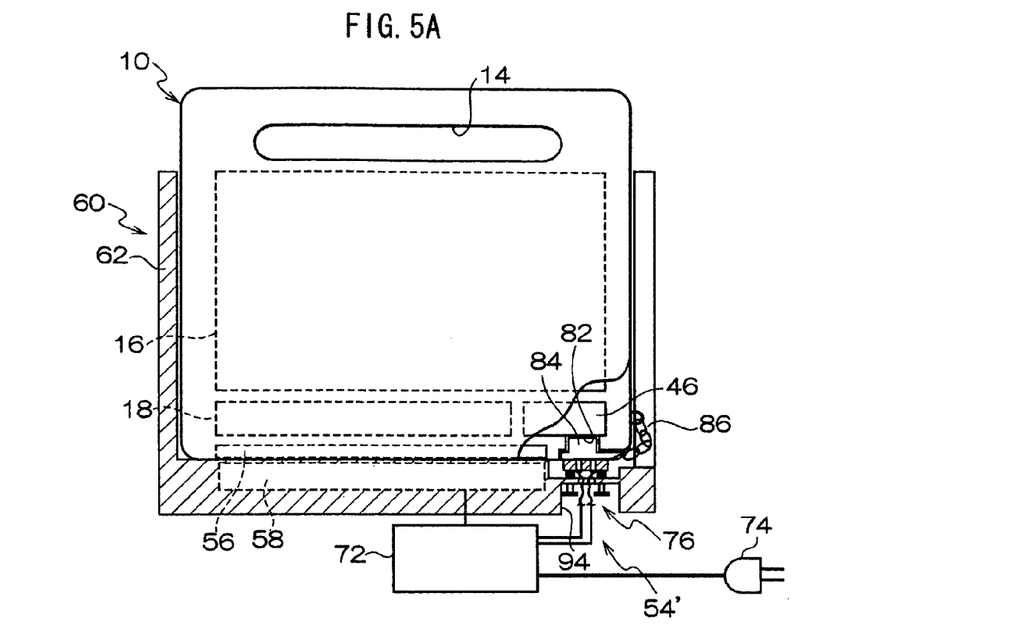
FIG. 5A shows a state in a normal charge mode.
Figure 5B:
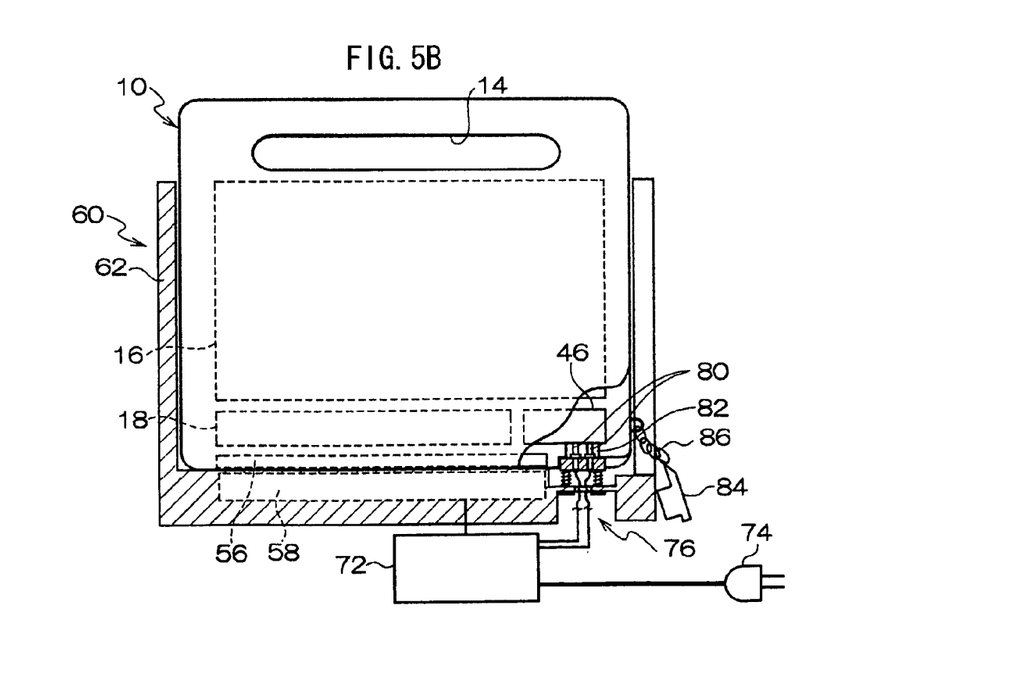
FIG. 5B shows a state in a quick charge mode.

As shown in FIGS. 5A and 5B, the primary coil unit 58 is disposed in a bottom portion of the pocket unit 62. The primary coil unit 58 is connected to a power supply unit 72 in the cradle 60. The power supply unit 72 is connected to a commercial power source through an electric outlet 74.

Therefore, the primary coil unit 58 receives the electric power supplied from the power supply unit 72, and the primary coil unit 58 converts the electric energy into the magnetic energy to transmit the magnetic energy to the secondary coil unit 56. The secondary coil unit 56 of the electronic cassette 10 converts the received magnetic energy into the electric energy to perform the electric power transmission. Accordingly, the power supply unit 46 of the electronic cassette 10 is charged without making the contact with the primary coil unit 58 (non-contact charge).

In the non-contact charge, a relatively long time is required for the charge because of low energy efficiency, and transmission processing speed being low during the charge. Such feature does not cause problems in cases where the electronic cassette 10 is normally used, that is, in cases where a charging time is sufficiently ensured.

On the other hand, in cases where the electronic cassette 10 is used again immediately after used for a long time (and after short interval), the power supply unit 46 is insufficiently charged. When the power supply unit 46 is insufficiently charged, image quality is deteriorated or a mistake of imaging is generated.

Therefore, in the exemplary embodiment, the electronic cassette 10 has a function of directly electrically connecting the terminal to perform the charge (contact charging function) in addition to the function of performing the charge by the electromagnetic induction (non-contact charging function). The contact charging function is not used in the normal state.

The charging device 54 which performs the contact charging function is provided in the bottom portion of the pocket unit 62 of the cradle 60 (see FIGS. 5A and 5B). A contact charging terminal unit 76 is connected to the charging device 54 through a lead wire 78.

The contact charging terminal unit 76 is disposed in a right end of FIG. 5 in the bottom portion of the pocket unit 62. In the electronic cassette 10, a pair of terminals 80 is projected from the power supply unit 46 so as to face the contact charging terminal unit 76. In the electronic cassette 10, a recess 82 is formed in the bottom portion at which the terminals 80 are projected. The terminals 80 are projected within the region of the recess 82.

A packing 84 is detachably attached to the recess 82. The packing 84 is connected to the electronic cassette 10 via a strap 86 such that the packing 84 is prevented from dropping out and being lost. When the packing 84 is fitted in the recess 82, the recess 82 becomes a closed space from the external. Therefore, the closed structure of the electronic cassette 10 is maintained when the contact charging function is not used.

The recess 82 is covered with a molded member 82A made of a polymer material such as an elastomer or a plastic by molding, and a gap with the housing 12 is closed (sealed). The packing 84 is a molded member made of a polymer material such as an elastomer or a plastic by molding. Examples of the elastomer include rubber or thermoplastic elastomer.

On the other hand, in a case where the contact charging function is used, the pair of terminals faces the contact charging terminal unit 76, when the electronic cassette 10 is loaded in the pocket unit 62 while the packing is removed. The contact charging terminal unit 76 includes a pair of electrodes 88 and a movable plate 90. The electrodes 88 are connected to the lead wire 78. The electrodes 88 are attached to an upper surface of the movable plate 90 so as to be projected.

The movable plate 90 is disposed on a partition base 96 provided in a through-hole 94 of the pocket unit 62. Pairs of round holes 98 are coaxially made in the partition base 96 and the movable plate 90, a pair of sliding pins 100 is inserted from below the partition base 96, and leading end portions of the sliding pins 100 are fixed to the movable plate 90.

Helical compression springs 102 are attached to the sliding pins 100 between the partition base 96 and the movable plate 90.

The movable plate 90 is biased toward a direction in which the movable plate 90 is pushed up with respect to the partition base 96 by the helical compression springs 102. At this point, when the electronic cassette 10 whose packing 84 is removed is loaded in the pocket unit 62, the pair of terminals on the side of the electronic cassette 10 is brought into electrical contact with the pair of electrodes on the side of the contact charging terminal unit 76, and the movable plate 90 is pushed down against the biasing forces of the helical compression springs 102 due to the relatively positional relationship between the electronic cassette 10 and the contact charging terminal unit 76, thereby ensuring a predetermined contact pressure.

On the other hand, in a case where the packing 84 is attached to the recess 82 of the electronic cassette 10, the packing 84 faces the pair of electrodes 88 when the electronic cassette 10 is loaded in the pocket unit 62.

In such a case, the packing 84 presses the movable plate 90. The movable plate 90 is pushed down against the biasing forces of the helical compression springs 102. At this point, a larger margin is ensured compared with the case in which the pair of terminals 80 presses the movable plate 90. Therefore, even if the electronic cassette 10 is loaded in the pocket unit 62 with the packing 84 attached, the electronic cassette 10 is located at the same position as the case in which the electronic cassette 10 is loaded with the packing 84 removed.

An operation of the exemplary embodiment will be described below.

As shown in FIG. 3, when taking the radiation image, the electronic cassette 10 is disposed so as to have a space between the electronic cassette 10 and the radiation generating unit 50 which generates the radiation such as an X-ray. At this point, the subject 52 is located between the radiation generating unit 50 and the electronic cassette 10 when taking the radiation image so this position is an image-take position for the subject 52. In response to an instruction to take the radiation image, the radiation generating unit 50 emits the radiation having a radiation dose according to predetermined shooting conditions and the like. The radiation emitted from the radiation generating unit 50 is transmitted through the subject 52 located at the image-take position, and the image information is carried by the radiation. Then the electronic cassette 10 is radiated with the radiation including the image information.

The image processing unit 24 processes the radiation image obtained by irradiating the imaging plate 16 of the electronic cassette 10 with the radiation, thereafter, the radiation image is transmitted to the image memory 18, and the radiation image is stored in the image memory 18.

The electronic cassette 10 may be grasped by the subject 52 so as to adjust a position to be taken, or a stand may be prepared to place the electronic cassette 10.

Thus, the electronic cassette 10 is portable, and the electronic cassette 10 is operated by the electric power charged in the power supply unit 46.

The capacitance amount of the power supply unit 46 is decreased when the electronic cassette 10 is used. When the capacitance amount is decreased, it is necessary to charge the power supply unit 46 of the electronic cassette 10. The electronic cassette 10 is charged by loading the electronic cassette 10 in the cradle 60 (normal charge, quick charge). When the charge is ended, the electronic cassette 10 can be used again.

Desirably the electronic cassette 10 is in closed state as much as possible, and the non-contact charging function in which the charge can be performed while the closeness is maintained is usually used for the electronic cassette 10 (normal charge). However, the non-contact charge in which a long charging time is required cannot respond to the case in which the electronic cassette 10 is urgently charged. Therefore, in the exemplary embodiment, the contact charge is performed to charge the electronic cassette 10 in an emergency (quick charge).

(Normal Charge)

In a case where the quick charge is not required, in order to maintain the closeness of the electronic cassette 10, preferably the electronic cassette 10 is charged only by the non-contact charging function without using the contact charging function. Therefore, in the normal state, the electronic cassette 10 is charged only by the non-contact charging function.

As shown in FIG. 5A, when performing the normal charge, the electronic cassette 10 is loaded in the pocket unit 62 of the cradle 60 while the packing 84 is closed.

Figure 6A:
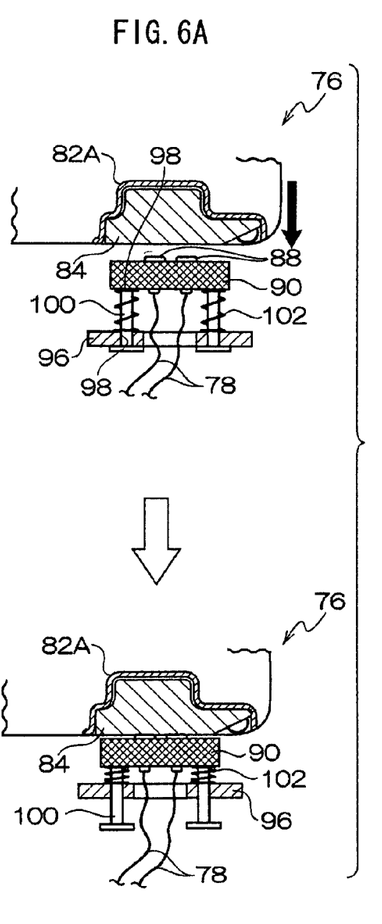
FIG. 6A shows a state in which a packing is attached.

At this point, as shown in FIG. 6A, the packing 84 of the electronic cassette 10 remains closed. The pair of terminals 80 is accommodated in the recess 82 while covered with the packing 84, therefore, the pair of terminals 80 on the side of the electronic cassette 10 is not brought into contact with the pair of electrodes 88 on the side of the cradle 60. Accordingly, the electronic cassette 10 is not charged from the contact charging terminal unit 76 on the side of the cradle 60.

Instead, the packing 84 attached to the recess 82 is brought into contact with the contact charging unit 76. The loading of the electronic cassette 10 in the pocket unit 62 is not disturbed because the contact charging unit 76 is pushed down along the sliding pins 100 against the biasing forces of the helical compression springs 102 (normal loading state).

When the electronic cassette 10 is normally loaded in the cradle 60, the secondary coil unit 56 of the electronic cassette 10 and the primary coil unit 58 of the cradle 60 face each other with a predetermined interval therebetween (non-contact). Therefore, the electric power of the commercial power source is supplied from the power supply unit 72 to the primary coil unit 58 through the electric outlet 74.

When receiving the electric energy, the primary coil unit 58 converts the electric energy into the magnetic energy to transmit the magnetic energy to the secondary coil unit 56 on the side of the electronic cassette 10.

When receiving the magnetic energy from the cradle 60, the secondary coil unit 56 converts the magnetic energy into the electric energy. The secondary coil unit 56 transmits the electric energy to the power supply unit 46 of the electronic cassette 10, and the electric energy is accumulated in the power supply unit 46 to complete the charge.

(Quick Charge)

On the other hand, in a case where the charging comes short in an emergency, the charging cannot be performed quickly only using the non-contact charging device 54. Therefore, the contact charging device 54 which has the high energy efficiency is used to charge the electronic cassette 10 (quick charge). When the contact charging device 54 is used, the electronic cassette 10 can quickly be charged so as to respond to the emergency.

As shown in FIG. 5B, when performing the quick charge, the electronic cassette 10 is loaded in the pocket unit 62 of the cradle 60 while the packing 84 is opened. The packing 84 remains in a state of being connected to the electronic cassette 10 via the strap 86.

Figure 6B:
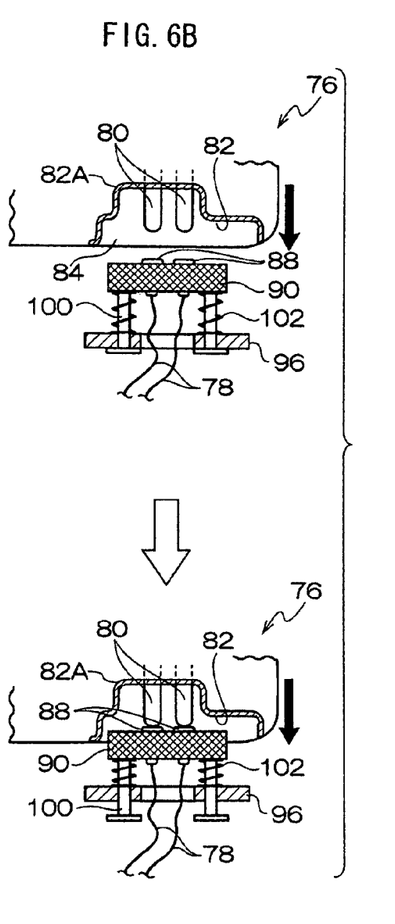
FIG. 6B shows a state in which the packing is detached.

As shown in FIG. 6B, when the electronic cassette 10 is loaded in the cradle 60, the pair of terminals 80 of the electronic cassette 10 and the pair of electrodes 88 of the cradle 60 are brought into electrical contact with each other.

At this point, the contact charging unit 76 is pushed down against the biasing forces of the helical compression springs 102. The contact failure is not occurred because the pair of electrodes 88 and the pair of terminals 80 are brought into contact with each other with a predetermined contact pressure due to repulsion forces (biasing forces) of the helical compression springs 102 when pushing down the contact charging unit 76.

By contacting between the pair of electrodes 88 and the pair of terminals 80, the power supply unit 46 is charged through the pair of electrodes 88.

Thus, in the exemplary embodiment, normally the electronic cassette 10 is loaded in the cradle 60 and the electronic cassette 10 is charged by the non-contact charging function. In the case of the contact charge, the pair of electrodes 88 and the pair of terminals 80 are brought into contact with each other by removing the packing 84, and the electronic cassette 10 is charged in a state where the wiring is physically connected. Therefore, the energy efficiency is improved compared with the non-contact charge and the charge is completed in a short time.

In the exemplary embodiment, it is switched between the normal charge and the quick charge by attaching and detaching the packing 84. Alternatively, the normal charge may automatically be switched to the quick charge by detecting the electric contact between the terminal 80 and the electrode 88.

In the exemplary embodiment, the charging functions of the contact charge and non-contact charge are separately used such that only contact charge is performed when contact charging and only non-contact charge is performed when non-contact charging. Alternatively, the non-contact charge may also be performed when contact charging.

In the exemplary embodiment, the electronic cassette 10 is loaded in the cradle 60 to charge the electronic cassette 10.

The invention is not particularly limited to the loading of the electronic cassette 10 in the cradle 60, but the electronic cassette 10 may be charged in other places except for the cradle 60 by using a portable charging adaptor.

In such cases, the contact charging terminal unit 76 attached to the cradle 60 may be detachably attached to the cradle 60.

In some electronic cassettes 10, a connect terminal 110, such as an IEEE1394 standard terminal (IEEE: Institute of Electrical and Electronics Engineers) or a USB terminal (see FIG. 7) is attached in order to access the outside to transfer the image recorded in the image memory 18. In such cases, the connect terminal 110 may be also used as the contact charging terminal.

In particular, the IEEE1394 standard terminal includes a version (for example, 6 pin connector type) having a relatively strong energy supplying capability (charging capability) of for example 8V-33V(Maximum) and 1.5 A, and therefore can be applied to the quick charging.

Figure 7:
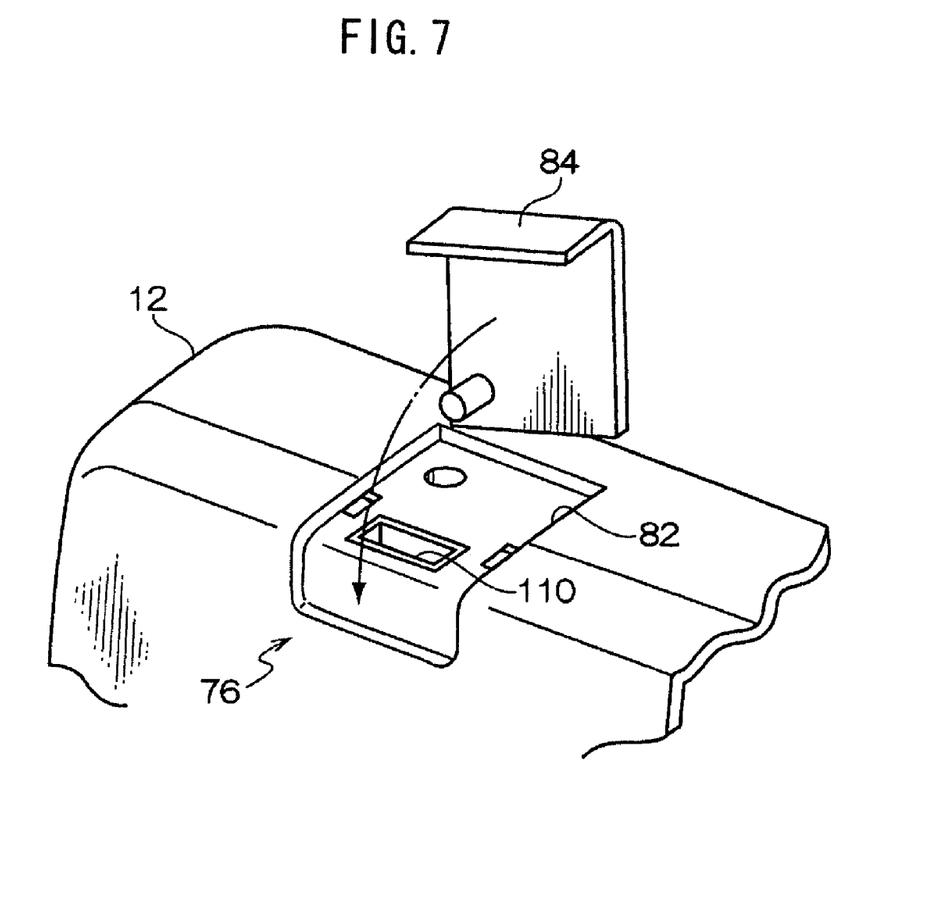
FIG. 7 is an enlarged perspective view showing a contact charge portion according to a modification of the exemplary embodiment.

Because the current USB has a standard of 5V and 500 mA (Max), the USB terminal 110 does not always withstand the quick charge. However, USB Implementers Forum proposes a USB standard (summarized in July, 2007) in which a current exceeding 500 mA can be supplied (that is, charged) (Battery Charging Revision 1.0). The application of Battery Charging Revision 1.0 can realize the quick charge using the USB terminal 110. The surrounding of the USB 110 terminal is usually closed by an elastomer or rubber, the closeness of the housing 12 is maintained in the normal use and in the non-contact charge. Regarding the IEEE1394 standard terminal, the closeness of the housing 12 can be maintained in the normal use and in the non-contact charge.

Note that another standard connect terminal other than the IEEE1394 standard terminal or the USB terminal may be formed in the electronic cassette 10 as the connect terminal by which the image recorded in the image memory 18 can be accessed from outside the housing 12 and the contact charging can be performed, as long as the closeness of the housing 12 can be maintained in the normal use and in the non-contact charge.

In the exemplary embodiment, the recess 82 is provided in the bottom portion of the housing 12. However, the recess 82 is not limited to the bottom portion. The recess 82 may be provided in a front face, a backside, a side face, an upper face of the housing 12. In cases where the cradle 60 is provided, preferably the recess 82 is located so as to face the charging device 54 when the electronic cassette 10 is loaded in the cradle 60.

What is claimed is:

1. A radiation imaging apparatus in which at least
   an imaging plate in which pixels which accumulate charges by receiving radiation are two-dimensionally arrayed, and which takes an image based on the received radiation,
   an image data memory in which data of the image taken by the imaging plate is stored, and
   a power supply unit that supplies electric power to the imaging plate and the image data memory,
   are accommodated in a closed housing, the radiation imaging apparatus comprising:
   a secondary coil unit provided in the housing and constituting a part of a non-contact type charging device, the secondary coil unit receiving an electric power by an electromagnetic induction effect between the secondary coil unit and a primary coil unit provided outside the housing;
   a terminal provided in the power supply unit, a leading end portion of which is projected outside the housing so as to be able to electrically contact an electrode of a contact type charging device provided outside the housing; and
   a closing member that is attachable to and detachable from the housing so as to be able to expose and close off the leading end portion of the terminal from the outside, the closing member maintaining a closed state of the housing when being attached to the housing, and putting the leading end portion of the terminal into an exposed state when being detached from the housing.

2. The radiation imaging apparatus of claim 1, wherein the power supply unit includes:
   a quick charging section that performs a quick charge mode for performing quick charging; and
   a normal charging section that performs a normal charge mode for performing non-quick charging, wherein
   contact charging by electrical contacting of contact-points is at least performed in the quick charge mode, and
   non-contact charging is performed in the normal charge mode.

3. The radiation imaging apparatus of claim 2, wherein switching between the quick charging section and the normal charging section is performed by attaching and detaching the closing member.

4. The radiation imaging apparatus of claim 2, wherein
   switching between the quick charging section and the normal charging section is performed based on electrical contact between the terminal and the electrode provided outside the housing,
   the quick charge mode is performed when the electrical contact is detected, and
   the normal charge mode is performed when the electrical contact is not detected.

5. The radiation imaging apparatus of claim 2, wherein both of the contact charging and the non-contact charging are performed in the quick charge mode.

6. The radiation imaging apparatus of claim 2, wherein
   the non-contact charging is performed by the primary coil unit provided outside the housing and the secondary coil unit provided in the housing, the primary coil and the secondary coil constituting parts of the non-contact type charging device, and
   the contact charging is performed by contacting the leading end portion of the terminal and the electrode of the contact type charging device provided outside the housing.

7. The radiation imaging apparatus of claim 1, wherein a recess portion is formed surrounding the terminal, and the closing member is attachable to the recess portion.

8. The radiation imaging apparatus of claim 1, wherein the closing member is connected to the housing via a connecting member.

9. A radiation imaging apparatus in which at least
   an imaging plate in which pixels which accumulate charges by receiving radiation are two-dimensionally arrayed, and which takes an image based on the received radiation,
   an image data memory in which data of the image taken by the imaging plate is stored, and
   a power supply unit that supplies electric power to the imaging plate and the image data memory,
   are accommodated in a closed housing, the radiation imaging apparatus comprising:
   a secondary coil unit provided in the housing and constituting a part of a non-contact type charging device, the secondary coil unit receiving electric power by an electromagnetic induction effect between the secondary coil unit and a primary coil unit provided outside the housing;

a connect terminal formed in the housing so as to be able to maintain a closed state of the housing, that is connected to the power supply unit and connected to the image data memory such that the data can be accessed from outside the housing, wherein contact charging can be performed via the connect terminal by a contact type charging device provided outside the housing; and a closing member that is attachable to and detachable from the housing so as to be able to expose and close off the leading end portion of the terminal from the outside, the closing member maintaining a closed state of the housing when being attached to the housing, and putting the leading end portion of the terminal into an exposed state when being detached from the housing.

10. The radiation imaging apparatus of claim 9 wherein the connect terminal is a USB terminal.

11. The radiation imaging apparatus of claim 9 wherein the connect terminal is an IEEE 1394 standard terminal.

12. A cradle in which a radiation imaging apparatus is accommodated, the radiation imaging apparatus having a closed housing in which at least (i) an imaging plate in which pixels which accumulate charges by receiving radiation are two-dimensionally arrayed, and which takes an image based on the received radiation, (ii) an image data memory in which data of the image taken by the imaging plate is stored, and (iii) a power supply unit that supplies electric power to the imaging plate and the image data memory, are accommodated, the radiation imaging apparatus including:

a secondary coil unit provided in the housing and constituting a part of a non-contact type charging device, the secondary coil unit receiving electric power by an electromagnetic induction effect between the secondary coil unit and a primary coil unit provided outside the housing;

a terminal provided in the power supply unit, a leading end portion of which is projected outside the housing so as to be able to electrically contact an electrode of a contact type charging device provided outside the housing; and a closing member that is attachable to and detachable from the housing so as to be able to expose and close off the leading end portion of the terminal from the outside, the closing member maintaining a closed state of the housing when being attached to the housing, and putting the leading end portion of the terminal into an exposed state when being detached from the housing, wherein the cradle includes an accommodation unit in which the radiation imaging apparatus is accommodated, the primary coil unit is disposed at a position in which the primary coil unit faces the secondary coil unit when the radiation imaging apparatus is accommodated in the accommodation unit, the electrode is disposed so as to be able to electrically contact the leading end portion of the terminal when the radiation imaging apparatus is accommodated in the accommodation unit, and when the radiation imaging apparatus is accommodated in the accommodation unit, the non-contact charging is applied when the closing member closes off the leading end portion of the terminal, and the contact charging is applied when the closing member exposes the leading end portion of the terminal.

* * * * *